United States Patent

Chatelier et al.

[11] Patent Number: 5,449,383
[45] Date of Patent: Sep. 12, 1995

[54] CELL GROWTH SUBSTRATES

[76] Inventors: Ronald C. Chatelier, 9 Apple Gve, Bayswater, Victoria 3168; Hans J. Griesser, 20 View Road, The Patch, Victoria 3792; John G. Steele, 7 The Carriageway, North Rocks, NSW 2151; Graham Johnson, 10 Moombara Avenue, Peakhurst, NSW 2210, all of Australia

[21] Appl. No.: 70,049

[22] Filed: Jun. 1, 1993

Related U.S. Application Data

[62] Division of Ser. No. 853,546, Mar. 18, 1992, abandoned.

[51] Int. Cl.⁶ .......................... A61F 2/06; A61F 2/54; C08J 7/18; C12N 11/08
[52] U.S. Cl. .......................... 623/1; 623/66; 427/2.24; 427/2.25; 427/255.6; 427/491; 435/173.4; 435/174; 435/177; 435/180; 428/407; 428/423.5
[58] Field of Search ............ 435/174, 180, 177, 173.4; 623/1, 66; 427/2.24, 2.25, 491, 255.6; 428/407, 423.5

[56] References Cited

U.S. PATENT DOCUMENTS

| | | | |
|---|---|---|---|
| 3,387,991 | 6/1968 | Erchak, Jr. | 427/40 |
| 3,449,154 | 6/1969 | Katz | 427/40 |
| 4,548,867 | 10/1985 | Ueno et al. | 427/569 |
| 4,919,659 | 4/1990 | Horbett et al. | 623/1 |
| 4,955,901 | 9/1990 | Nishiguchi et al. | 427/491 |
| 5,007,928 | 4/1991 | Okamura et al. | 427/491 |

FOREIGN PATENT DOCUMENTS 1242166 9/1988 Canada .
0133832 3/1985 European Pat. Off. .
2101608 1/1983 United Kingdom .
WO91/16378 10/1991 WIPO .

OTHER PUBLICATIONS

Derwent Abs 88–068438/10 Abs (J63023935)(Oct. 1988), Mitsui Toatsu.
Derwent Abs 4–253392/41 Abs (J59152913)(Aug. 1984) Ikada.
Derwent Abs 84–154798/25 Abs (J59080443)(May 1984) Toyo Soda Mfg KK.
Patents Abstracts of Japan, C–239, p. 157, Abstract 59–80443 (1984).
Derwent Abstract Accession No. 84–253392/41 (1984).
Patents Abstracts of Japan, C–508, p. 88, Abstract 63–23935 (1988).

*Primary Examiner*—Herbert J. Lilling
*Attorney, Agent, or Firm*—Birch, Stewart, Kolasch & Birch

[57] ABSTRACT

A process for producing a polymeric surface coating which faciliates attachment of cells on a polymeric substrate. The coating is deposited by plasma deposition of an amide monomer vapour. The coated product is suitable for use in tissue culture trays and biomedical implants.

11 Claims, 8 Drawing Sheets

CELL GROWTH SUBSTRATES

This application is a divisional, of application Ser. No. 07/853,546 filed on Mar. 18, 1992, now abandoned.

BACKGROUND OF THE INVENTION

1. Field of the Invention

This invention relates to cell growth substrates that possess improved properties with regard to the attachment and growth of cells. The invention relates to the production of novel cell growth substrates from materials that possess suitable bulk properties, but inappropriate surface chemical composition for good attachment and growth of cells. In a particular aspect the materials and method of this invention are useful for the fabrication of substrates for attachment and growth of human cell lines.

Good attachment and growth of cells on the surfaces of an artificial implant are critical for applications such as vascular grafts. However, human cells generally show little tendency to attach and grow evenly on the surface of articles made from polymeric materials. To overcome this deficiency, a number of modifications to the bulk polymer or the polymer surface have been described in the art. The synthesis of bulk polymers is one approach; another is the surface modification of known polymers to provide chemical groups that confer improved performance on the polymer surface. It is important to be able to optimize both the bulk properties and the surface properties with some degree of independence, and surface modification procedures are well suited to this aim.

2. Description of the Related Art

The interaction between a polymeric material and biomedical constituents such as proteins and cells occurs at the polymer surface. The interfacial forces are very short range, and therefore are determined by the chemical constituents at the surface and in the sub-surface region of the polymeric material, that is, chemical groups located within only a few molecular layers of the surface of the polymeric material. Surface modification techniques are thus ideally suited to the control of polymer properties governed by interfacial interactions, such as for biomedical applications. The growth of human cells on tissue culture dished is strongly dependent on the chemical composition of the polymer surface (Griesser, Johnson and Steele, Polymeric Materials Science and Engineering, in press), and it is presumed that the growth of endothelial cells inside a vascular graft following implantation is likewise affected by the composition of the polymer surface of the graft. A number of surface treatment techniques for polymeric materials are known in the art: Corona Discharge, Flame Treatment, Acid Etching, and a number of other methods intended to perform chemical modification of the surface. Disadvantages of these techniques comprise the use of or production of hazardous chemicals, the often excessive depth of treatment, non-uniformity of treatment at a microscopic level, and often severe etching and pitting that leads to changes in surface topography. The depth of treatment is important because with thin polymeric materials such as those required for small diameter vascular grafts the bulk properties soon become affected by an excessive treatment.

Treatment of polymeric surfaces by gas plasmas presents the advantages of very low treatment depth and uniformity on a microscopic scale. A gas plasma (also known as glow discharge) is produced by electrical discharge in a gas atmosphere at reduced pressure ("vacuum"). It creates a stable, partially ionized gas that may be utilized for effecting reactions on the surface of the polymer substrate because the gas plasma environment activates even chemical compounds that are unreactive under normal conditions. The treatment intensity at the surface is generally relatively strong, and yet, the penetration depth of gas plasma treatment is very low, of the order of 5 to 50 nanometres, at a treatment level sufficient for useful surface modification. Surface topography does not change unless exposure to the plasma is performed for extended periods of time usually much exceeding the time required for achieving the desired chemical modification. There occurs, therefore, much less alteration of the properties of the bulk polymer than with alternative treatment technologies.

A glow discharge in an oxygen containing atmosphere has been claimed to render polymeric surfaces more hydrophilic (U.S. Pat. No. 4,452,679). The treatment leads to formation of polar, oxygen containing functionalities on the surface. The main disadvantage of this approach is that the treatment is not permanent due to reorientation of the polymer chains with time because polymeric materials undergo unavoidable, thermally driven chain segmental motions. Wettability by water decreases as the hydrophilic surface groups produced by treatment become buried inside the polymer, as described by H. Yasuda et. al. in J. Polym. Sci.: Polym. Phys. Ed., 19 1285 (1981). The hydrophilic nature of the surface thus diminishes with storage time. Another disadvantage is that, such surfaces are not good substrates for cell attachment and growth per se, but they require the provision of an adhesion promoting protein prior to cell attachment and growth. An example of this is the surface modification of polystyrene, which has enabled the successful fabrication of cell culture dishes ("tissue culture polystyrene", TCP) which support good attachment and growth of human cells, but only if the dishes are precoated with adhesive protein such as fibronectin (C. Klein-Soyer, S. Hemmendinger and J. P. Cazenave, Biomaterials 1989, Vol. 10, 85). In the absence of pre-coating, cells grown on top look patchy and irregular.

Other hydrophilic surface modification procedures have been utilized in order to improve the attachment and growth of cells on tissue culture dishes and vascular grafts and the like articles where performance is dependent on good cell anchorage. The modification of surfaces in an ammonia plasma has been described and seems to provide cell compatible surfaces. However, chemical groups attached to the surface in this way are subject to the same thermally driven reorientation, which means that the newly created surface groups are slowly lost from the surface. Surface modification techniques are needed that provide permanent surface compositions and good cell response.

Tissue culture dishes provide a convenient means of studying the process of attachment and growth of cells, and it is considered that the surface treatment procedures suitable for the optimization of cell culture dishes are also suitable for the optimization of surgical implant materials. One cell growth substrate is available (Falcon Primaria tissue culture plate) which does not require pre-coating with absorbed adhesive protein. The reason for this is stated to be the incorporation of amine and amide groups into the polystyrene chain. Primaria does, however, suffer from the disadvantage that the adhesion of the extracellular matrix to the polymer surface is not strong, and that repair of lesions is slower that on other TCP dishes.

In spite of the considerable literature on cell growth substrates, the problem of providing stable surfaces on polymeric articles such that human cells attach and grow well without requiring the step of pre-coating with adhesive protein, the extracellular matrix adheres well, and cells are able to readily execute repair to any damage, has not yet been solved.

SUMMARY OF THE INVENTION

Accordingly, in one aspect, the present invention provides a polymeric material having on at least a part of its surface a thin polymeric layer which is suitable for supporting cell growth wherein said polymeric layer comprises reorientation resistant polymer chains presenting amide groups for the attachment of cells. Any bulk polymeric material which is capable of accepting a stable second polymeric layer by a plasma polymerisation process is suitable. Such bulk polymeric materials may be natural and synthetic addition condensation polymers and also include but are not limited to perfluorinated polymers, polyethylene, polyesters, polyurethaners copolymers thereof and mixtures thereof.

In a second aspect, the invention provides a method of cell growth comprising growing cells upon a polymeric material according to the first aspect of the present invention.

In a third aspect, the invention provides a tissue culture dish comprised of a polymeric material according to the first aspect of the present invention.

In a fourth aspect, the present invention provides a biomedical implant comprising a polymeric article having thin polymeric coating layer on at least a portion of its surface, said polymeric coating layer providing reorientation resistant polymer chains presenting amide groups for the attachment of cells.

In a further aspect, the present invention provides a substrate for cell attachment and growth, said substrate comprising a polymeric material wherein a surface of said polymeric material bears a layer formed by plasma polymerization in the presence of one or more organic monomeric compounds selected from amides or mixtures thereof.

DETAILED DESCRIPTION OF THE INVENTION

The cell growth substrates of this invention may be multilayer materials fabricated by the application of a thin layer coated by plasma polymerization on to a conventional material that serves as the bulk of the multilayer composite.

Dimethylacetamide and dimethlyformamide are examples of two very suitable amides.

The plasma polymerization process serves to incorporate amide groups into the surface layer of the culture substrate in order to obtain good attachment and growth of human cells. In contrast to the surfaces produced by plasma modification with ammonia plasma, the surfaces fabricated by plasma polymerization of amides are relatively stable and thus present an improvement over the existing art. The cell growth substrates produced according to the present invention allow the attachment and growth of human cells without requiring pre-coating by adhesive protein and they also show superior performance in the adhesion of cells and in the repair of lesions.

The invention also provides biomedical implants which have been produced according to the invention.

In further aspects, the invention provides a process for the preparation of multilayer polymeric materials which process includes providing a polymeric substrate and depositing a surface layer on said substrate by plasma polymerisation of a vapour composition containing at least one plasma polymerisable amide monomer. If desired intermediate layers may be deposited between said substrate and said surface layer or further layers of any suitable material may be applied to said surface layer.

The plasma polymerisable vapour may include more than one amide. It may also include other organic compounds, or appropriate additives and inorganic gases.

Amides suitable for the performance of the invention include compounds of the structure $R^1$—CO—$N(R^2)R^3$ where $R^1$ is an aliphatic, alicyclic or aromatic group which may optionally contain one or several halogen atoms, hydroxyl groups and the like, and $R^2$ and $R^3$ may each be hydrogen or a saturated alkyl group such as methyl, ethyl or propyl.

Alternatively, the organic amide vapour stream may be formed in situ from precursors.

Other organic compounds such as organic amines may optionally be used in the vapour phase of the invention, to give a mixed monomer vapour, provided that at least one of the compounds in the mixed vapour phase of the invention is an organic amide compound.

Examples of inorganic gases which may be used in association with the plasma process to control the resultant thin layer composition include oxygen, argon, hydrogen, etc., Argon is particularly useful in assisting the evaporation and plasma ignition of compounds with low vapour pressure.

Figure 1:
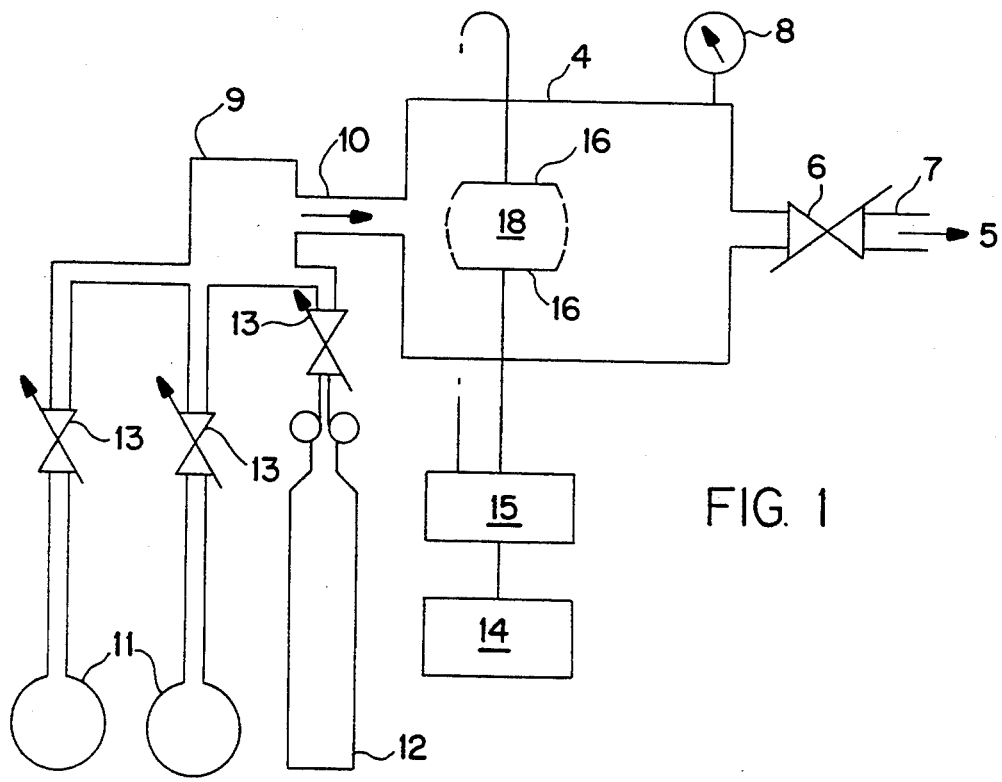
FIG. 1 is a schematic view showing the parts of a plasma polymerization apparatus for performing the process of this invention.
Figure 5:
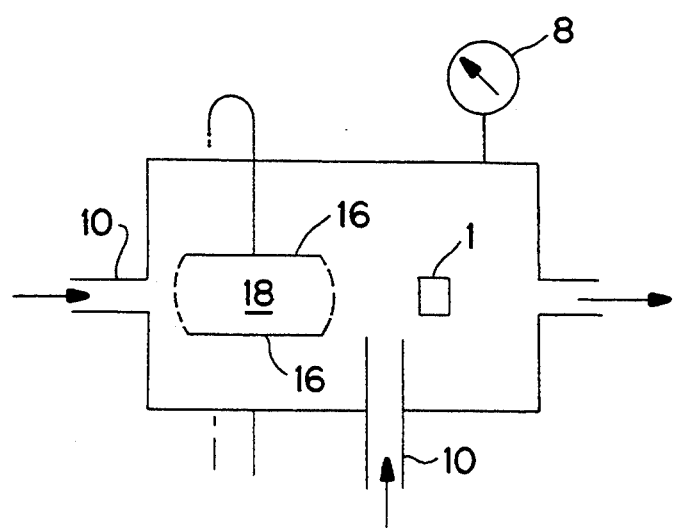
FIG. 5 is a schematic view of an embodiment of the present invention using two streams of vapor or gas.
Figure 6:
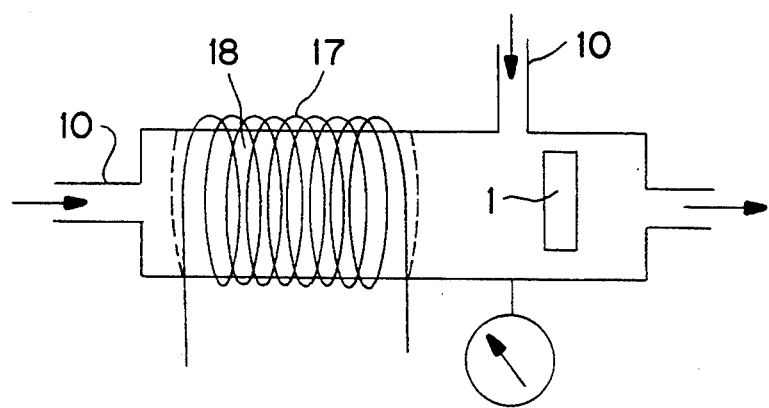
FIG. 6 is a schematic view of an embodiment of the present invention where the vapor stream is activated by a coil.
Figure 7A:
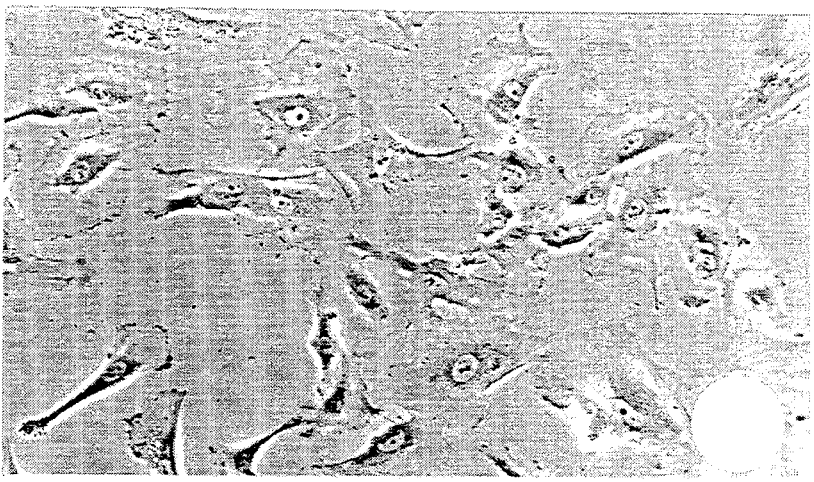
FIGS. 7A, 7B, 7C, 7D, 7E, 7F, 7G, 7H, 7I, 7J, 7K, and 7L show the difference in morphology of human umbilical artery endothelial cells cultured on prior art materials, and materials of the claimed invention.
Figure 7B:
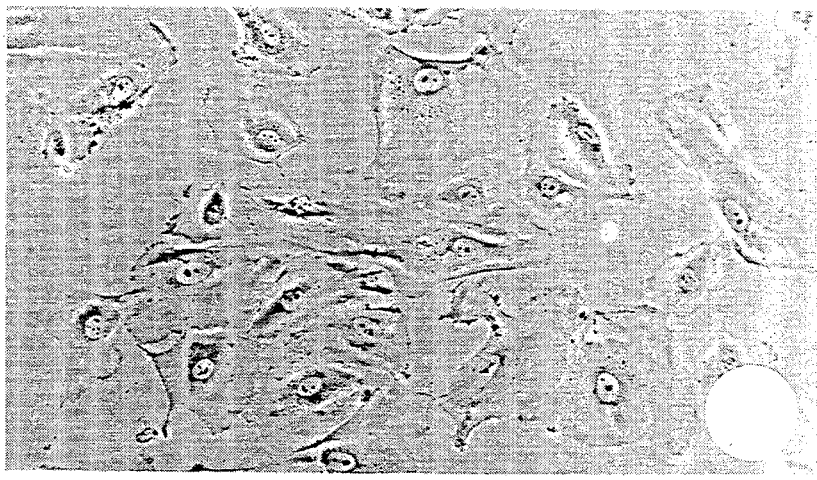
Figure 7C:
Figure 7D:
Figure 7E:
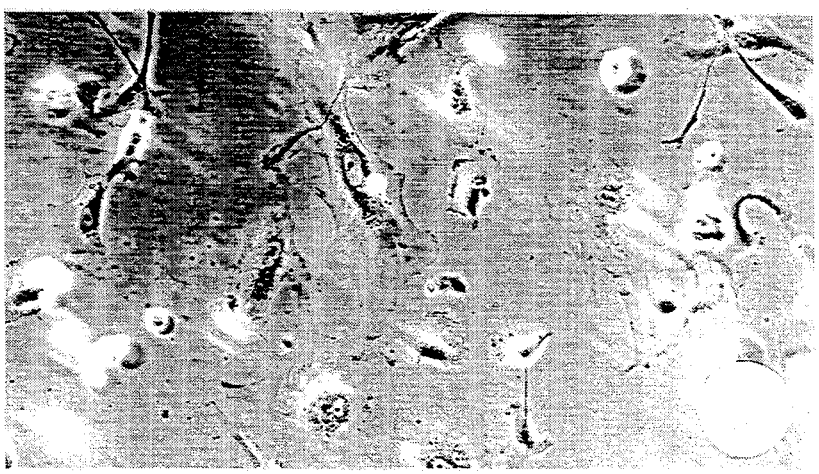
Figure 7F:
Figure 7G:
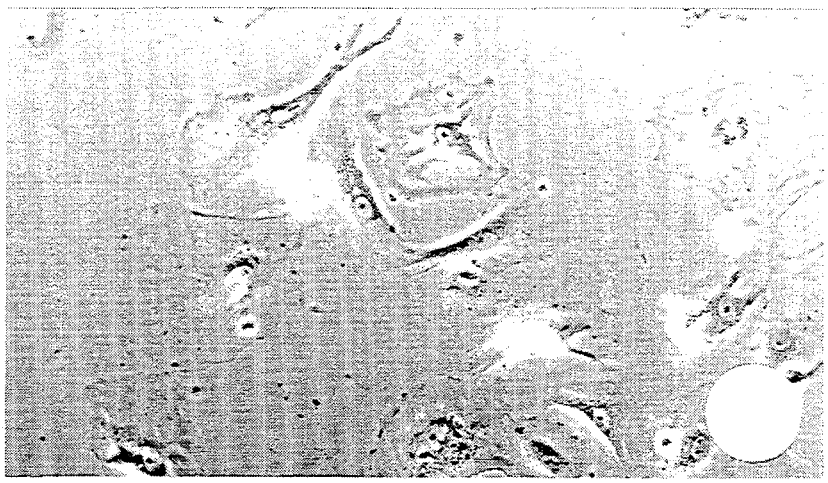
Figure 7H:
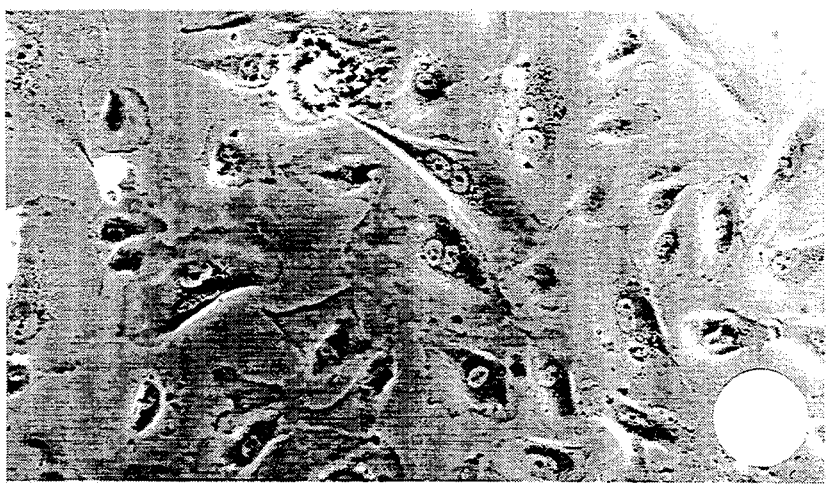
Figure 7I:
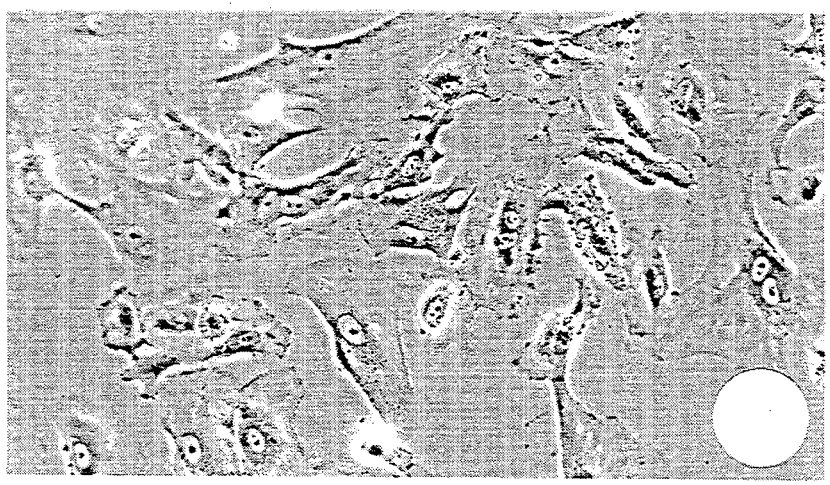
Figure 7J:
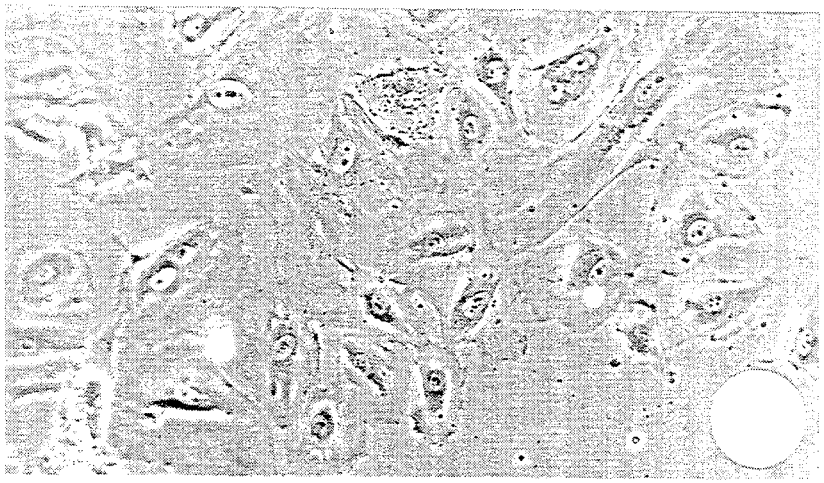
Figure 7K:
Figure 7L:
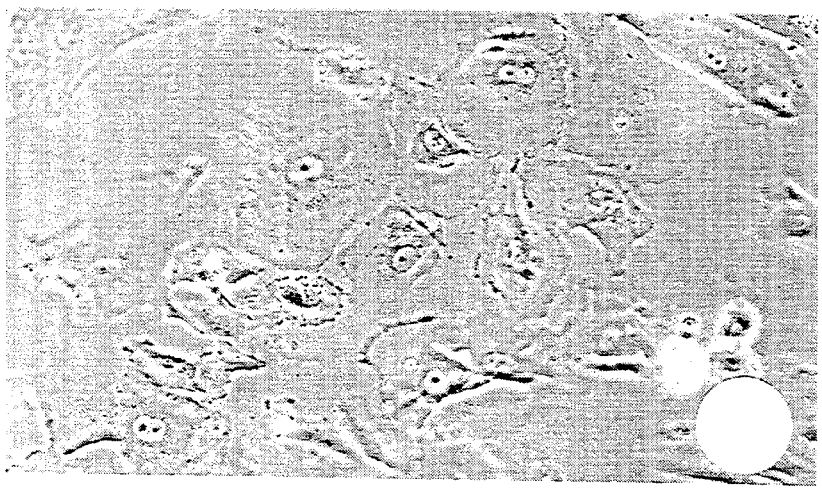

When vapour of more than one chemical compound is used in the process of the invention, the mixing of vapours can be done in several ways. The streams of two or more vapour and gas components may be united prior to reaching the electric discharge zone in an embodiment as shown in FIG. 1. In other embodiments of the invention at least one of the streams passes through an electric discharge zone and becomes excited by partial ionization, while at least one other stream does not pass through a discharge zone and is admixed in an unexcited state to the other, excited vapour stream, and the mixture is then directed to the bulk polymeric material 1 for thin layer formation, as shown in FIGS. 5 and 6. When three or more chemical components are used, any combination thereof is possible, provided at least one vapour becomes electrically excited.

The thin layer produced by plasma polymerization from a monomer vapour containing vapour of at least one of the specified compounds and optionally other organic compounds and/or inorganic gasses effects a modification of the surface of the bulk polymeric material 1 by the application of the thin layer, which is stable with time. The multilayer cell growth substrates of the invention thus retain good mechanical and other bulk properties while excelling by improved cell response. The thin layer may be 5 nm–10 $\mu$m thick, more preferably the thin layer may be 50–500 nm thick.

The invention will be now further explained by referring to the embodiments shown in the accompanying figures.

FIG. 1 is a schematic view showing the parts of a plasma polymerization apparatus 3 for performing the process of this invention. A vacuum chamber 4 is evacuated by a pumping system 5 connected by an adjustable throttle valve 6 and an exhaust pipe 7. The pressure in the chamber is monitored by a pressure gauge 8. Vapour and gas streams are supplied to a mixing device 9 and reach the vacuum chamber 4 via an inlet pipe 10. Preferably, pressures of 0.5–1.0 torr are used.

Organic monomer liquids are stored in thermostatted containers 11. Evaporation by boil off supplies organic vapour. Inorganic gases, such as argon and oxygen, are supplied from cylinders 12. All streams are individually controlled by flow control equipment 13 prior to reaching the mixing device 9. All streams may be used singly or in any combination.

High frequency electric power is provided by a source 14 via a matching network 15 to the electrodes 16. On application of electric power a discharge is established in the discharge zone 18 between the electrodes and as a result, the vapour becomes activated. From the gas plasma the activated products of organic monomer or monomers are polymerized as a thin layer 2 on to one or multiple surfaces of the bulk polymeric material 1.

Figure 2:
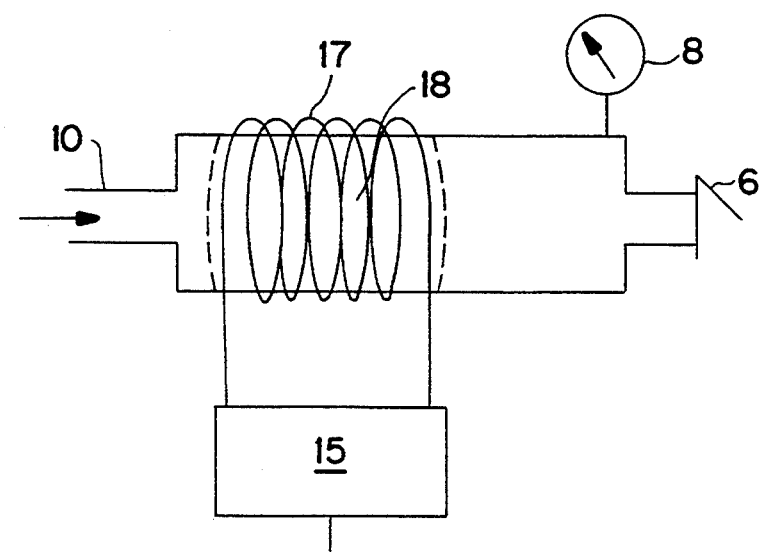
FIG. 2 is a schematic view of a modified process according to the present invention.

FIG. 2 is a schematic view of a modification of the process of this invention. The apparatus is the same as in FIG. 1 except that the high frequency electric power is supplied to a coil 17 and no electrodes are provided.

Figure 3:
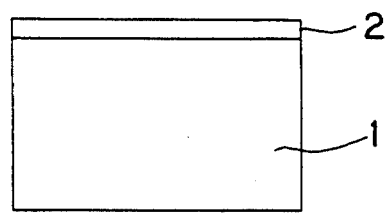
FIG. 3 is a cross-sectional view of a rectangular material according to the present invention.
Figure 4:
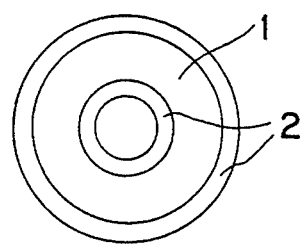
FIG. 4 is a cross-sectional view of a tube-shaped material according to the present invention.

FIGS. 3 and 4 schematically show several embodiments of the multilayer polymeric products of this invention. FIG. 3 shows a thin layer 2 applied to one or several faces of a bulk polymeric material 1 of rectangular cross-section. FIG. 4 shows a schematic cross-section through a tube-shaped bulk polymeric material 1 that has a thin plasma polymer layer 2 both on the inside and the outside. The invention is not restricted to the embodiments shown.

FIG. 5 is a schematic view of an embodiment of the process of this invention using two streams of vapour or gas. Each of the streams may direct one or several vapour components to the vacuum chamber via its inlet pipe. As in FIG. 1 the organic vapours and inorganic gases are controlled and mixed prior to the inlet pipe. One of the two streams is fed through the electric discharge zone 18 and the other stream is added to the vacuum chamber downstream of the discharge zone. FIG. 6 shows another embodiment of the process where one vapour stream is activated by a coil 17. The process of the invention is not restricted to the particular embodiments shown; three or more inlet pipes may be provided.

FIG. 7 shows the difference in morphology (determined by phase contrast microscopy) of human umbilical artery endothelial cells cultured on the material of example 1, tissue culture polystyrene (panels a–d), on example 2 Primaria tissue culture plastic (panels e–h), and on example 4, FEP plasma modified with dimethylformamide (panels i–l). The cells were cultured for 1 day (panels a, b, e, f, i, j) or for 3 days (panels c, d, k, l) or for 4 days (panels g, h). The surfaces shown in panels b, d, f, h, j and l were precoated with fibronectin prior to seeding of cells. The culture medium for all surfaces included intact serum.

Figure 8:
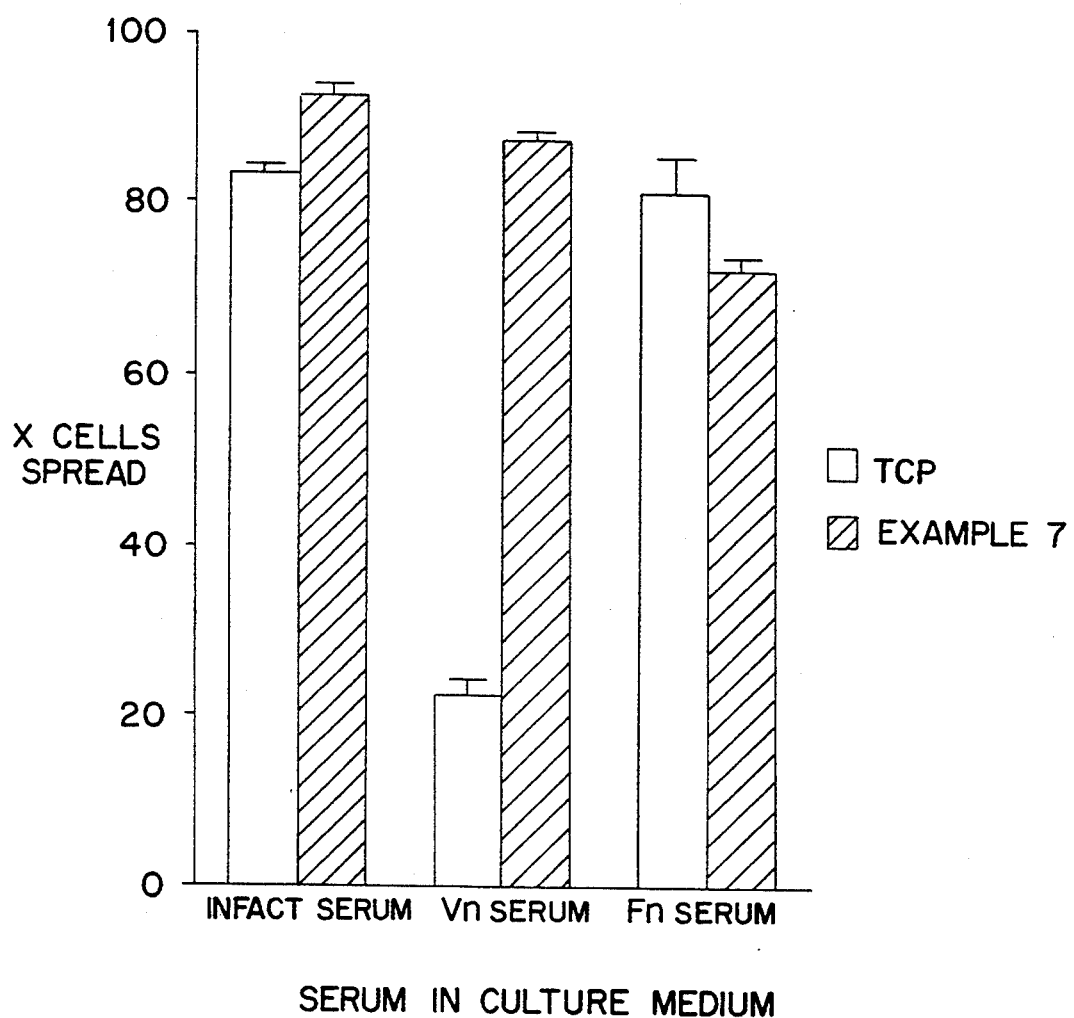
FIG. 8 is a histogram showing the proportion of HUAE cells that become attached and spread onto TCP and plasma-modified surfaces.

FIG. 8 is a histogram showing the proportion of HUAE cells that became attached and spread onto TCP (example 1) and plasma-modified (example 5) surfaces during the 4 hours following seeding in culture medium containing intact serum, or serum depleted selectively of fibronectin, or depleted selectively of vitronectin. (Mean, +SEM of triplicate determinations).

Examples of the polymeric materials of this invention will be explained below together with comparative examples.

COMPARATIVE EXAMPLES 1 TO 3

Comparative example 1 was Corning tissue culture polystyrene. Comparative example 2 was Falcon Primaria cell wells. Comparative example 3 was fluorinated ethylene propylene copolymer.

EXAMPLES 4 TO 5

Figure 1A:
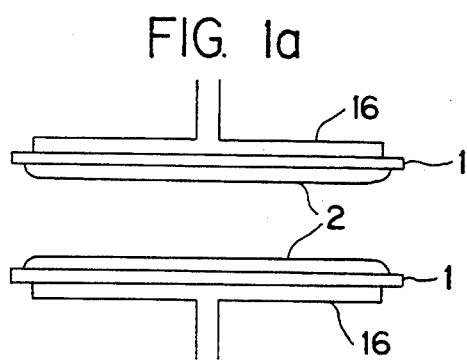
FIG. 1a shows an electrode arrangement for plasma polymerization wherein the thin layer is applied to a polymer surface parallel to the electrode surfaces.
Figure 1B:
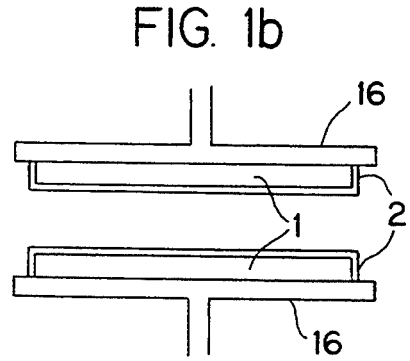
FIGS. 1b and 1c show electrode arrangements for plasma polymerization wherein the layer is applied to polymer surfaces that are parallel and perpendicular to the electrode surface.
Figure 1C:
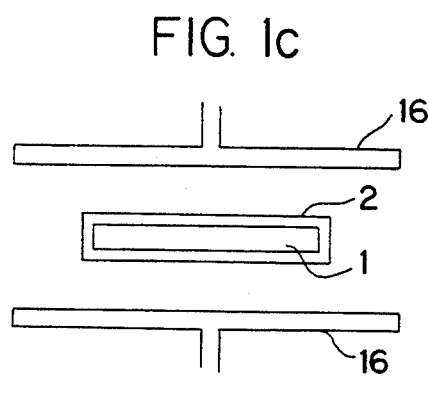
Figure 1D:
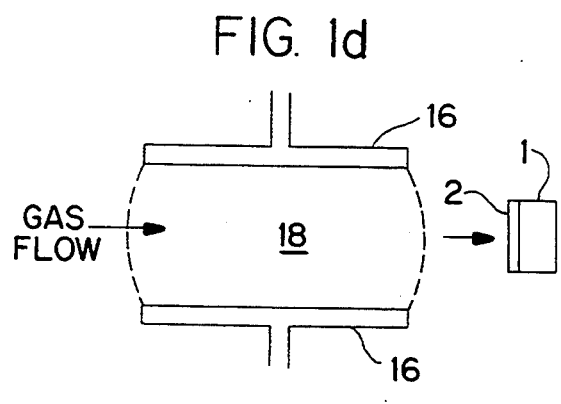
FIG. 1d shows an electrode arrangement for plasma polymerization wherein the polymer surface is not between the electrodes.

Multilayer cell growth substrates were prepared using the apparatus as shown in FIG. 1. Fluorinated ethylene propylene copolymer was used as the bulk polymeric material 1 and attached to the electrodes as in FIG. 1a. For example 4, vapour of dimethylformamide was supplied by evaporating from the liquid held in a container. Before ignition of the plasma, the vapour was pumped through the reactor and system for several minutes. A plasma polymer layer 2 was then deposited from the vapour onto the surface of the bulk material 1. Example 5 was fabricated in the same way but using dimethylacetamide vapour. In both cases the plasma was ignited for a duration sufficient to produce a coating to a thickness of the layer 2 in the range of 50 to 500 nm.

Cell attachment and growth: the attachment, spreading and growth of human endothelial cells onto the modified and onto the control unmodified fluoropolymer surfaces was determined as an indication of the value of the surface modification methods outlined in this patent application for the production of surfaces of potential use in biomaterial and biotechnological applications. Human endothelial cells (HUAE cells) were derived from umbilical arteries and used as the cell strain for attachment and growth assays. It has been our previous experience that the ability of a surface to support the attachment, spreading and growth of HUAE cells is a stringent test of the general usefulness of that surface for growth of tissue cells (including not merely other endothelial cells but also cells of mesenchymal or epithelial origin). HUAE cells were seeded onto surfaces that had been plasma modified by the methods described for examples 4 to 5 and compared to HUAE cell attachment and growth on:

Example 1, hydrophilic "tissue culture" polystyrene (TCP, from Corning Glass Works, Corning, N.Y.); Example 2, Primaria tissue culture substrate, (from Becton Dickinson and Company, Lincoln Park, N.J.); and Example 3, unmodified fluorinated ethylene propylene (FEP).

Sample preparation and cell assay conditions: The samples of examples 4 to 5 were prepared for cell attachment assays by sonication in a solution of 70% Ethanol at 24 um for 20 seconds per sample, then rinsed in sterile phosphate-buffered saline solution. Samples were then transferred to serum-free culture medium "Medium 199" for equilibration (at least 1 hour incubation) prior to commencing the cell assay. The plasma-modified side of the film was exposed to the cells in the assay. The HUAE cells were derived from umbilical arteries and established in culture by the methods of Jaffe et. al., (1973) and used between passages 5 to 7. These HUAE cells were confirmed to show positive immunostaining for von Willebrand's factor (Factor VIII—related antigen). The cells were routinely maintained in a growth medium consisting of Medium 199 (Flow laboratories) supplemented with 20% v/v foetal bovine serum (Cytosystems, Sydney), 60 ug/ml endothelial cell growth supplement (Collaborative Research), 100 ug/ml porcine heparin (Sigma Chemical Co.,) 60 ug/ml penicillin (Glaxo) and 100 ug/ml streptomycin (Glaxo) on TCP coated with fibronectin (coated with a 40 ug/ml solution of bovine fibronectin at 37° C. for 1 hour prior to use).

HUAE cells became attached, spread and grew when seeded on to TCP (example 1), Primaria (example 2) or the surfaces of examples 4 to 5, see FIG. 7 and Table 1 below. The morphology of the attached cells when attached to sample surfaces was taken as an important indicator of the suitability of the surfaces for cell attachment and growth, as only surfaces that do permit HUAE cells to spread well also permit good cell growth. Some attachment of HUAE cells was observed on unmodified FEP (example 3) but these cells had a spindle-like, fibroblastoid morphology that is characteristic of unsatisfactory endothelial cell attachment, grew poorly, and lifted off the surface after 3 days of culture. To obtain the attachment, spreading, and growth of HUAE cells onto TCP (example 1), Primaria (example 2) and plasma-modified surfaces (examples 4 to 5) it was necessary to use a cell culture medium that contained serum. This indicates a need for the culture medium to contain serum adhesive glycoprotein to become absorbed onto the polymeric surface and participate in HUAE cell attachment and spreading onto that surface. There are two such serum components, fibronectin (Fn) and vitronectin (Vn), see Grinnell (1976), Exp. Cell Res., 97, 265-274; Underwood and Bennett, (1989) J. Cell Sci., 93, 641-649; Norris et. al. (1990), J. Cell Sci., 95-255-262). The roles of fibronectin and vitronectin in the attachment of HUAE cells onto TCP (example 1) and onto plasma-modified surfaces (e.g. example 5) was determined by the selective removal of serum fibronectin and vitronectin from the serum component of the culture medium (see Underwood and Bennett (1989) and Norris et. al., (1990) for methods), and comparing the attachment in this culture medium with attachment in medium containing intact serum. FIG. 8 shows that the serum component vitronectin is required for the initial attachment and spreading of HUAE cells onto TCP and that removal of vitronectin from the serum used in the culture medium inhibited the attachment and spreading of the HUAE cells over the first 3 hour period of culture, see also Norris et. al., (1990). In contrast, removal of vitronectin from the serum in the culture medium in which HUAE cells were seeded onto a plasma-modified surface (e.g. example 5 is shown in FIG. 8) failed to inhibit initial cell attachment and spreading. Removal of serum from the culture medium in which HUAE cells were seeded failed to inhibit HUAE cell attachment and spreading onto TCP or the plasma-modified FEP (example 5).

In previous studies it has been shown that when TCP (e.g. example 1) is used as a culture substratum, the attachment and growth of human endothelial cells may be enhanced by pretreatment of the TCP surface with a solution of fibronectin purified from serum and the HUAE cells were routinely maintained on Fn-coated TCP. The assays of the suitability of the plasma-modified surfaces for cell attachment were also conducted using samples of the surfaces which had been precoated with fibronectin. Coating with Fn was achieved by incubating the samples with a solution of 40 ug/ml Fn in PBS at 37° C. for 1 hour prior to cell seeding. Excess solution was removed before cells were added.

Table 1 below summarizes the results of the assays of the examples, both with and without prior coating with fibronectin. The morphology of the HUAE cells was determined after 1, 3 and 5 days of culture, and a semi-quantitative assessment of the suitability of the surfaces for HUAE cell attachment and growth, based upon the number and morphology of the attached cells, was made:

The HUAE cells failed to attach to example 3, the unmodified FEP film. Thus any cell attachment that occurred to examples 4 to 5 without pre-coating with purified Fn, would indicate that the plasma-modified surface was more suitable for cell attachment than the unmodified surface. The plasma-modified surfaces supported HUAE cell attachment and growth to an extent that was clearly improved over the untreated control FEP, and enabled cell attachment and spreading to a level approximately equivalent to that on TCP. Each of the FEP (example 3) and FEP modified by plasma modification (examples 4 to 5) supported HUAE cell attachment and growth when precoated with fibronectin prior to cell seeding and these cells showed a well spread morphology. The cells seeded onto FEP (example 3) coated with fibronectin grew for 3 days in culture, but tended to become detached after a further period in culture, whereas the plasma-modified surfaces (examples 4 to 5), whether coated with fibronectin or not, supported HUAE cell growth over a 7 day period with the cells coming to form a confluent monolayer.

The morphology of HUAE cells attached to the surfaces of examples 4 to 5, as viewed after 3 days after cell seeding, was equivalent to that on TCP, i.e. the HUAE cells attached to the surface of examples 4 to 5 when seeded in the presence of serum and spread, but it should be noted that the cells had not formed the well spread morphology that is typical of HUAE cells that have been seeded onto Fn-coated TCP. For the Fn-coated examples 4 to 5, the number of cells attached and the morphology of the attached cells was equivalent to that on the Fn-coated TCP.

These results clearly demonstrate that the plasma-modified surfaces support cell attachment, spreading and growth of human endothelial cells. These surfaces are therefore suitable for inclusion as components in implants where good cell interactions with the surface is required, and for use in in vitro cell culture applications.

TABLE 1

| Surface | Cell Growth Data | |
|---|---|---|
| | Fn precoating | Assessment |
| Example 1 (TCP) | no | 3+ |
| | yes | 5+ |
| Example 2 (Primaria) | no | 3+ |
| Example 3 (FEP) | no | 0 to 0.5+ |
| | yes | 3+ |
| Example 4 | no | 3+ |
| | yes | 5+ |
| Example 5 | no | 4+ |
| | yes | 5+ |

Cell growth data showed that cell responses were equivalent to that on the examples 4 to 5 made by plamsa-deposition onto the FEP substratum.

Tables 2 and 3 demonstrate the stability or instability of plasma coatings produced from dimethylacetamide (DAC) and ammonia. Stability is demonstrated by stable sessile contact angle (SCA) measurements taken over a period of time. A contact angle is considered stable within an experimental accuracy of ±3 degrees.

TABLE 2

| SCAs on Plasma Treated Surface, Ammonia Plasma | |
|---|---|
| Time (days) | SCA (degrees) |
| 0 | 16 |
| 3 | 21 |
| 7 | 32 |
| 18 | 37 |
| 43 | 43 |
| 67 | 56 |

The Contact Angle is not stable, indicating that changes are occuring over time.

TABLE 3

| SCAs on Plasma Polymers Fabricated From Dimethylacetamide, freshly prepared and after 2-½ months storage in air. | | |
|---|---|---|
| Sample | Fresh SCA | Stored SCA |
| 1 | 35 | 38 |
| 2 | 33 | 36 |
| 3 | 36 | 39 |

Other aspects of the present invention, and modifications and variations thereto, will become apparent to those skilled in the art on reading this specification, and all such other aspects and modifications and variations are to be considered to be included within the scope of the present invention.

We claim:

1. A polymeric material comprising:

(A) a substrate comprising a bulk polymeric material; and (B) a thin polymeric layer which is suitable for supporting cell growth, comprising a reorientation resistant polymer comprising plasma-polymerized amide monomers presenting amide groups for the attachment of cells, wherein said amide monomers are selected from the group consisting of dimethyl formamide and amides having the formula $$R^1-CO-N(R^2)R^3$$

wherein $R^1$ is an aliphatic, alicyclic, or aromatic group, each of which may be optionally substituted by halogen atoms or hydroxy groups, and $R^2$ and $R^3$ are each independently hydrogen or an alkyl group, and wherein said thin polymer layer promotes attachment and proliferation of said cells.

2. A polymeric material suitable as a support for cell growth, which has been produced by providing a substrate comprising a bulk polymerization material and depositing a surface layer on said substrate by plasma polymerization of a vapor composition containing at least one plasma polymerizable amide monomer selected from the group consisting of dimethyl formamide and amides having the formula $$R^1-CO-N(R^2)R^3$$

wherein $R^1$ is an aliphatic, alicyclic, or aromatic group, each of which may be optionally substituted by halogen atoms or hydroxy groups, and $R^2$ and $R^3$ are each independently hydrogen or an alkyl group, and wherein said surface layer promotes attachment and proliferation of said cells.

3. A biomedical implant comprising the polymeric material of claim 1.

4. A biomedical implant comprising the polymeric material of claim 2.

5. The polymeric material according to claim 1, wherein said material is suitable as a support for the growth of human endothelial cells.

6. The polymeric material according to claim 2, wherein said material is suitable as a support for the growth of human endothelial cells.

7. The polymeric material according to claim 1, wherein said bulk polymeric material is a natural or synthetic addition condensation polymer.

8. The polymeric material according to claim 1, wherein said bulk polymeric material is selected from the group consisting of perfluorinated polymers, polyethylene, polyesters, polyurethanes, and copolymers and mixtures thereof.

9. The polymeric material according to claim 1, wherein said substrate further comprises intermediate layers between said bulk polymeric material and said thin polymer layer.

10. The polymeric material according to claim 1, wherein said reorientation resistant polymer further comprises plasma-polymerized organic amine monomers.

11. A process for producing a biomedical implant, comprising shaping a biomedically suitable polymeric material into an implant shape under dust-free, sterile conditions, and depositing thereon a surface layer by plasma polymerization of a vapor composition containing at least one plasma polymerizable amide monomer.

* * * * *